(12) United States Patent
Griffin et al.

(10) Patent No.: US 10,335,195 B2
(45) Date of Patent: Jul. 2, 2019

(54) PERCUTANEOUS ACCESS SYSTEMS AND METHODS

(71) Applicant: Summit Access, LLC, Englewood, CO (US)

(72) Inventors: Dennis Griffin, Englewood, CO (US); Leroy D. Geist, Aurora, CO (US); LeRoy Jutte, Highlands Ranch, CO (US)

(73) Assignee: Summit Access, LLC, Englewood, CO (US)

( * ) Notice: Subject to any disclaimer, the term of this patent is extended or adjusted under 35 U.S.C. 154(b) by 210 days.

(21) Appl. No.: 14/946,514

(22) Filed: Nov. 19, 2015

(65) Prior Publication Data
US 2017/0143937 A1    May 25, 2017

(51) Int. Cl.
| | |
|---|---|
| *A61M 25/00* | (2006.01) |
| *A61B 17/34* | (2006.01) |
| *A61M 25/06* | (2006.01) |
| *A61M 25/01* | (2006.01) |

(52) U.S. Cl.
CPC ..... *A61B 17/3439* (2013.01); *A61M 25/0074* (2013.01); *A61M 25/0606* (2013.01); *A61B 2017/3454* (2013.01); *A61M 25/0105* (2013.01)

(58) Field of Classification Search
CPC ...... A61M 2025/0024; A61M 25/0069; A61M 25/0136
See application file for complete search history.

(56) References Cited

U.S. PATENT DOCUMENTS

| | | | | |
|---|---|---|---|---|
| 3,565,074 A | * | 2/1971 | Foti | A61M 25/0606 604/164.11 |
| 3,619,529 A | | 11/1971 | Nealis | |
| 4,772,266 A | * | 9/1988 | Groshong | A61M 25/0668 604/160 |
| 4,785,826 A | | 11/1988 | Ward | |
| 5,217,468 A | | 6/1993 | Clement | |
| 5,267,572 A | | 12/1993 | Bucalo | |

(Continued)

OTHER PUBLICATIONS

United States Patent and Trademark Office Acting as the International Searching Authority, "International Search Report and Written Opinion," dated Jan. 13, 2016, in international application No. PCT/US2015/059058.

(Continued)

*Primary Examiner* — Rebecca E Eisenberg
*Assistant Examiner* — Tasnim Mehjabin Ahmed
(74) *Attorney, Agent, or Firm* — Durham Jones & Pinegar, P.C., Intellectual Property Law Group

(57) ABSTRACT

Percutaneous access systems, including trocars, for accessing desired locations within a subject's body through the subject's skin or other tissues that are configured to minimize incision sizes are disclosed. Such a percutaneous access system includes a cannula and an obturator. The cannula includes a passageway with a tapered section and an expandable section at its distal end. The expandable section may include leaves that are configured to extend radially outward as an elongated instrument that has an outer diameter that exceeds a minimum relaxed inner diameter of the tapered section of the passageway is forced through the tapered section. Methods for using such a percutaneous access system, including medical procedures, are also disclosed.

15 Claims, 5 Drawing Sheets

(56) References Cited

U.S. PATENT DOCUMENTS

| | | |
|---|---|---|
| 5,364,365 A | 11/1994 | Wortrich |
| 5,385,151 A | 1/1995 | Scarfone et al. |
| 5,573,008 A | 11/1996 | Robinson et al. |
| 5,792,074 A | 8/1998 | Turkel et al. |
| 5,807,282 A | 9/1998 | Fowler |
| 5,817,033 A | 10/1998 | DeSantis et al. |
| 5,823,970 A | 10/1998 | Terwilliger |
| 5,843,031 A | 12/1998 | Hermann et al. |
| 5,885,226 A | 3/1999 | Rubinstein et al. |
| 5,910,121 A | 6/1999 | Paolo et al. |
| 6,176,834 B1 | 1/2001 | Chu et al. |
| 6,716,216 B1 | 4/2004 | Boucher et al. |
| 6,758,824 B1 | 7/2004 | Miller et al. |
| 7,144,386 B2 | 12/2006 | Korkor et al. |
| 7,803,142 B2 * | 9/2010 | Longson ............. A61M 25/065 604/158 |
| 8,262,619 B2 | 9/2012 | Chebator et al. |
| 8,764,679 B2 | 7/2014 | Miller et al. |
| 9,282,948 B2 | 3/2016 | Melchiorri et al. |
| 9,351,710 B2 | 5/2016 | McGhie et al. |
| 2004/0030319 A1 * | 2/2004 | Korkor ............. A61M 25/0662 604/506 |
| 2005/0080430 A1 * | 4/2005 | Wright, Jr. ........ A61B 17/22031 606/108 |
| 2009/0306586 A1 | 12/2009 | Ross et al. |
| 2012/0265097 A1 | 10/2012 | Melchiorri et al. |
| 2014/0163418 A1 | 6/2014 | Gigi |

OTHER PUBLICATIONS

United States Patent and Trademark Office Acting as the International Searching Authority, "International Search Report and Written Opinion," dated Feb. 5, 2016, in international application No. PCT/US2015/061662.

* cited by examiner

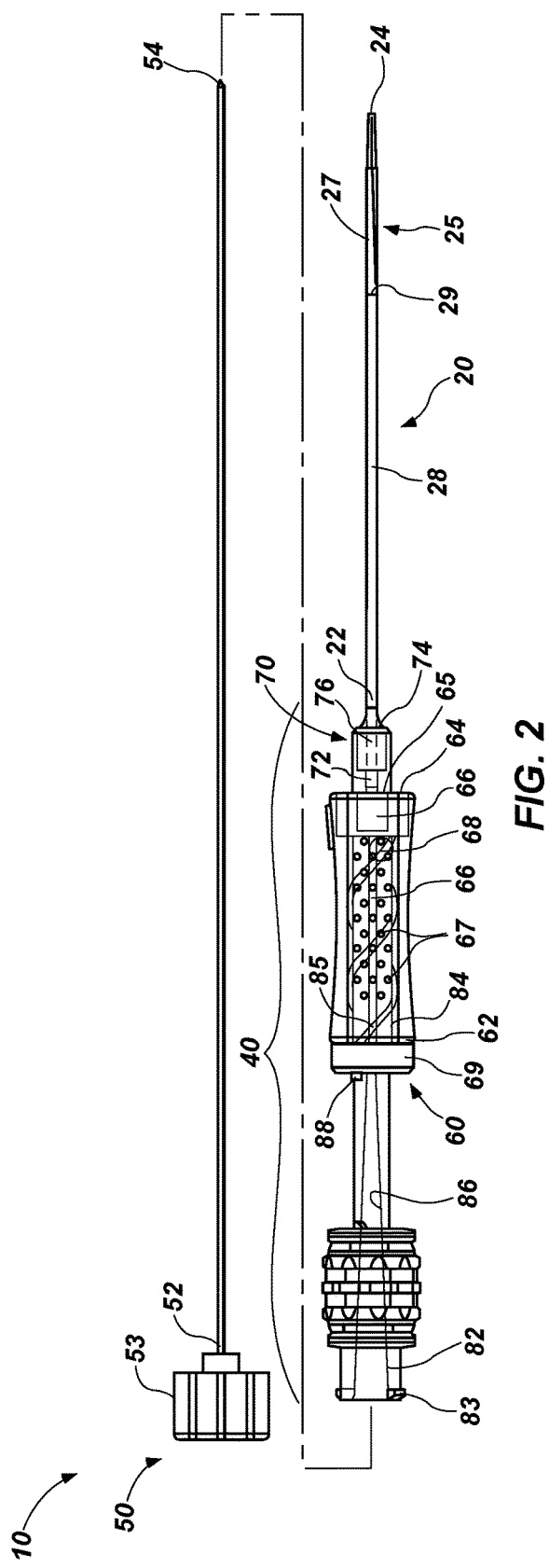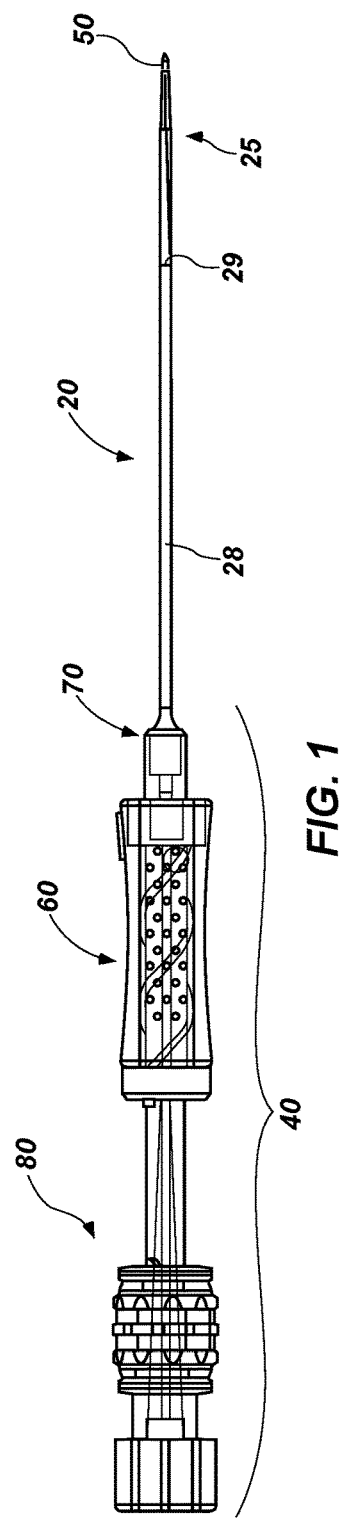
FIG. 1
FIG. 2

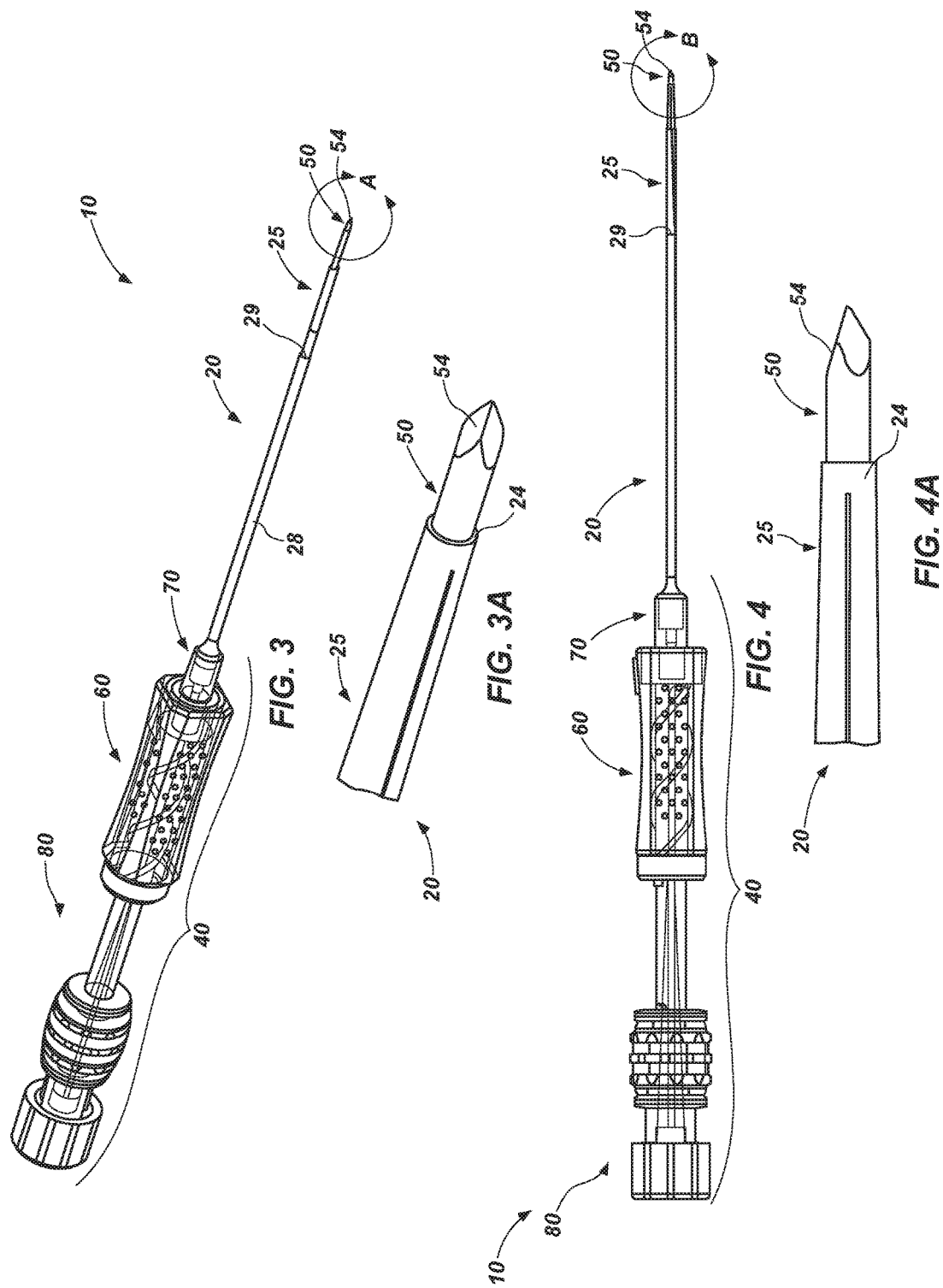

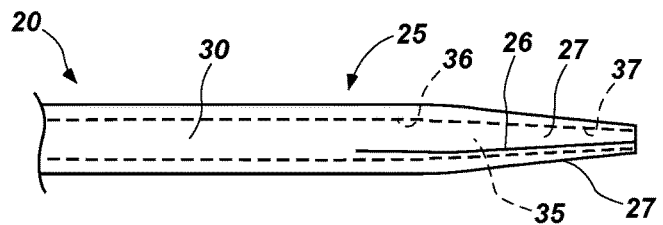
FIG. 5
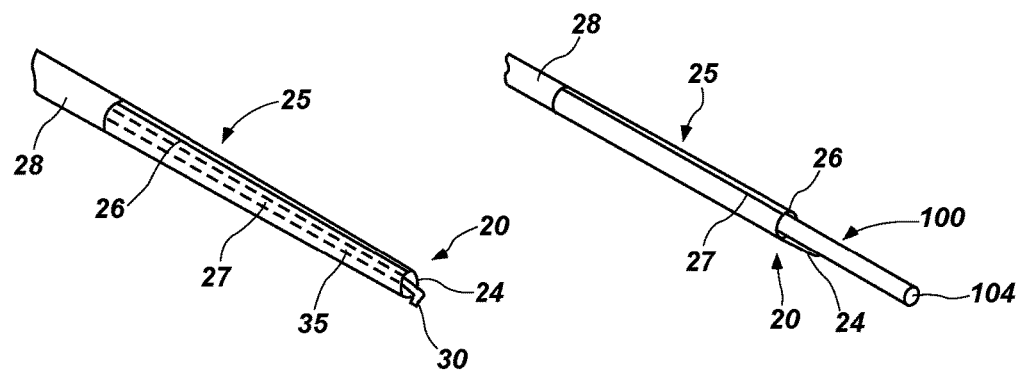
FIG. 6         FIG. 7

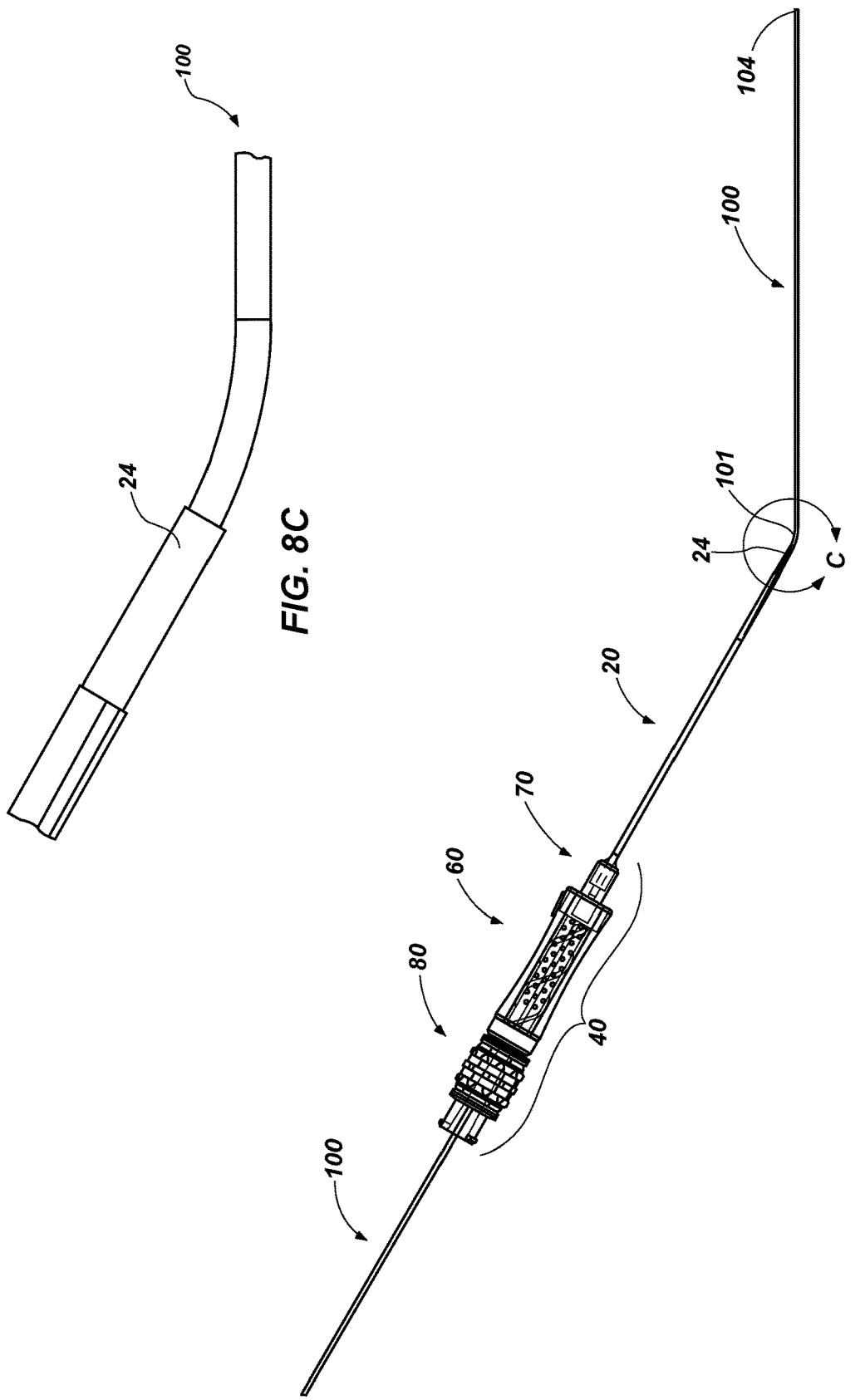

PERCUTANEOUS ACCESS SYSTEMS AND METHODS

TECHNICAL FIELD

This disclosure relates to percutaneous access systems and, more specifically, to percutaneous access systems, including trocars, with cannulas that are configured to minimize the dimensions of an opening through skin. Additionally, this disclosure relates to methods for using percutaneous access systems.

RELATED ART

Trocars have been employed in the medical field for many years. A trocar typically includes a cannula (a hollow tube), an obturator with a sharpened tip that extends through a channel of the cannula, and a seal between the obturator and the cannula. The sharp top of the obturator, when extended from a distal end of the cannula, is configured to form an incision, or opening, through a subject's skin or other tissues and, thus, to be introduced into a site of interest (e.g., a location through which a laparoscopic procedure is to be performed, etc., such as a cavity, a blood vessel, etc.) within the subject's body. Once the sharp tip of the obturator and the distal end of the cannula have been positioned at the location of interest, the obturator may be removed from the channel of the cannula and the laparoscopic procedure may then be performed through the cannula.

The distal end of the cannula of a conventional trocar typically has a fixed outer diameter, which is usually consistent with the outer diameter of a remainder of the cannula. Thus, the size of the incision made by the obturator must accommodate the outer diameter of the cannula. In embodiments where the channel of the cannula must accommodate medical instruments with relatively large outer diameters, a cannula with a larger outer diameter is required and, thus, a relatively large incision must be made through the subject's skin or other tissues.

Large incisions are typically undesirable for a number of reasons. For example, larger incisions are typically more unsightly than smaller incisions, take longer to heal than smaller incisions, result in an undesirable amount of scar tissue relative to the amount of scar tissue generated as a subject heals from a smaller incision, and pose a greater risk of infection from the procedure and as the subject heals from the procedure.

SUMMARY

This disclosure, in various aspects, relates to enhancements to existing procedures that involve the use of trocars. In addition, this disclosure relates to "percutaneous access systems," including trocars, for accessing desired locations within a subject's body through the subject's skin with minimal incision sizes.

In one aspect, a percutaneous access system comprises a trocar with a tapered cannula that includes an expandable section at its distal end. In some embodiments, the cannula may include an elastomeric sheath over a proximal portion of the expandable section. The expandable section may include an external taper from a relatively large outer diameter at a proximal location to a smaller outer diameter at a more distal location, as well as an internal taper (along an internal passageway that extends through the cannula) from a relatively large inner diameter at a proximal location to a smaller inner diameter at a more distal location. Slits (e.g., laser cuts, etc.) along the length of the expandable section at various locations around the circumference of the expandable section may separate the expandable section into a plurality of expandable elements (each of which is also referred to herein as a "leaf"), and may enable expansion of the expandable section.

In addition to the tapered, expandable cannula, a trocar according to this disclosure includes an obturator. The obturator is configured to be inserted from a proximal side of the cannula into and through the cannula, such that a distal tip of the obturator will extend through and protrude from a distal end of the cannula. A distal tip of the obturator may be configured to pierce the skin and/or other tissues of a subject's body to provide access to a desired location within the subject's body. More specifically, the distal tip of the obturator may comprise a sharpened point or a sharpened edge, which may be configured to pierce skin or other tissues of the subject and, thus, to form an incision, or opening, and, optionally, a pathway through the skin and/or one or more other tissues of the subject's body. In some embodiments, an outer diameter of the obturator may be the same as or slightly smaller than a smallest inner diameter of the cannula, enabling the obturator to be completely introduced into and assembled with the cannula, and to protrude from a distal end of the cannula, without causing the distal end of the cannula to expand. Thus, the obturator may form an incision and the unexpanded, tapered distal end of the cannula may follow the distal tip of the obturator into the incision. Alternatively, the obturator may have an outer diameter that exceeds the smallest inner diameter of the cannula, in which case the obturator may be proximally withdrawn through the cannula to enable the distal end of the cannula to contract as it is advanced distally into the incision.

The obturator may be removed from the cannula to make way for another elongated instrument, such as a laparoscopic surgical instrument, a guidewire, a sheath, a tube and/or a catheter. An outer diameter of the elongated instrument may be less than the relatively large inner diameter of the cannula but, in some embodiments, greater than the smaller inner diameter of the cannula. As an elongated instrument with an outer diameter that exceeds the smaller inner diameter of the cannula is introduced distally through the internal passageway through the cannula, the elongated instrument will force leaves of the expandable section outward, putting the expandable section into an expanded state, in which both the inner diameter and the outer diameter of the distal portion of the expandable section of the cannula are effectively increased. In some embodiments, the portion of the internal passageway of the cannula that extends through the expandable section may be configured to open gradually as the distal end of the elongated instrument moves therethrough, with the expandable section only opening completely when the distal end of the elongated instrument is coincident with the distal end of the cannula. As the outer diameter of the expandable section increases, an opening through any tissues (e.g., skin, etc.) in which the expandable section is located may be dilated, or enlarged.

When a portion of the elongated instrument that has forced the leaves of the expandable section of the cannula outward is removed from the expandable section (e.g., withdrawn from the internal passageway in a proximal direction, etc.), the leaves may be free to collapse, enabling the expandable section of the cannula to return to its initial collapsed state. The presence of an elastic sleeve, if any, around the proximal portion of the expandable section may ensure that the leaves return to their initial orientations and, thus, that the expandable section returns to its collapsed state. As the expandable section of the cannula collapses, the opening(s) in tissues through within which the expandable section resides may also constrict, or return to its (their) initial, smaller size(s).

In another aspect, a percutaneous access system, such as a trocar, may include a cannula with an expandable section, an obturator (e.g., a rigid obturator; a flexible, or bendable, obturator; etc.) insertable into and/or movable through the cannula, an optional elongated instrument (e.g., a wire, a sheath, a tube, a catheter, a laparoscopic surgical instrument, etc.), and a housing for maintaining a relationship between the cannula and the obturator or other elongated instrument. The housing may include a distal hub secured to a proximal end of the cannula, a proximal hub configured to engage a proximal portion of the obturator and/or a location along a length of another elongated instrument (e.g., a wire, a sheath, a tube, a catheter, a laparoscopic surgical instrument, etc.), and a main body to which the distal hub and the proximal hub are secured. The distal hub may be fixedly secured in place relative to a distal side of the main body. In some embodiments, the proximal hub may be rotatably secured in place relative to a proximal side of the main body. More specifically, a retaining ring may be configured to be fixedly secured in place relative to the proximal side of the main body of the housing, while holding the proximal hub in place, and enabling the proximal hub and, thus, the elongated instrument to rotate relative to the main body, the distal hub and the cannula. In some embodiments, the proximal hub may be configured to be grasped between an individual's thumb and finger (e.g., index finger, etc.) to enable manual manipulation of the elongated instrument. One or both of the retaining ring and the main body may be configured to enable or cause the proximal hub and the elongated instrument to rotate and/or otherwise move relative to the main body in a controlled fashion (e.g., along a helical thread, along a spiral groove, etc.). In some embodiments, the retaining ring and/or the main body may be configured in a manner that enables the proximal hub to lock in one or more positions (e.g., in a proximal position (i.e., with the elongated instrument fully withdrawn (proximally) into the cannula), in one or more intermediate positions, in a distal position (i.e., with the elongated instrument fully extended (distally) from the cannula), etc.). The proximal hub can be locked into a distal position as the distal end of the elongated instrument protrudes from the distal end of the cannula.

The proximal hub of a percutaneous access system according to this disclosure may include a passage extending through its length. The passage through the proximal hub may be continuous with and, thus, communicate with the internal passageway through the cannula. The passage through the proximal hub may be configured to receive an elongated instrument that may also extend into and/or through the internal passageway through the cannula. In some embodiments, the proximal hub (e.g., the passage therethrough, etc.) may be configured to engage the elongated instrument and, thus, cause the elongated instrument to rotate about its longitudinal axis as the proximal hub is rotated about the longitudinal axes of the housing and/or the cannula.

An access technique according to this disclosure may include introducing an obturator of a trocar into and through a cannula of the trocar in such a way that a distal end of the obturator, which is configured to cut and/or puncture a subject's skin, protrudes from (and, thus, beyond) a distal end of the cannula. With a longitudinal position of the obturator fixed relative to a longitudinal position of the cannula, the obturator may be positioned against the subject's skin at a location that is intended to form an incision, or opening, and provide access to a site of interest, and then forced into and at least partially through the subject's skin. The obturator and a distal and of the cannula may then be advanced to a desired location within the subject's body (e.g., a vascular location, a non-vascular location, etc.), creating a path that will provide access to the desired location. Once the desired location has been accessed, the obturator may be withdrawn into the cannula and from the percutaneous access system. Another elongated instrument, such as a laparoscopic surgical instrument, a wire, a sheath, a tube and/or a catheter, may be introduced into and through the internal passageway through the cannula. In embodiments where an outer diameter of the elongated instrument exceeds the smaller inner diameter of the expandable section of the cannula, movement of the elongated instrument distally through the expandable second may cause the expandable section to expand, which may dilate, or stretch, one or more openings in tissues through which the expandable section extends rather than requiring the formation of a larger opening or the use of a more complex conventional dilation system.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 1 is a side view of an embodiment of percutaneous access system according to this disclosure, which percutaneous access system comprises a trocar;

FIG. 2 is an exploded view showing various elements of the embodiment of percutaneous access system of FIG. 1, in which the elongated instrument comprises an obturator that is configured to be assembled with a housing and a cannula of the percutaneous access system;

FIGS. 3 and 4 provide isometric view of the embodiment of percutaneous access system shown in FIG. 1;

FIGS. 3A and 4A provide enlarged view of the sections identified as "A" and "B" of FIGS. 3 and 4, respectively;

FIG. 5 illustrates an embodiment of an internal passageway through an expandable section of a cannula, which includes at least one taper;

FIGS. 6 and 7 are perspective views of an expandable section of the cannula and an elastic sleeve that surrounds a proximal portion of the expandable section, respectively showing the expandable section in collapsed and expanded states; and FIGS. 8A-8C illustrate an embodiment of percutaneous access system in which the housing and cannula are used in conjunction with an elongated instrument, such as a laparoscopic surgical instrument, a wire, a sheath, a tube, or a catheter.

DETAILED DESCRIPTION

Figure 8A:
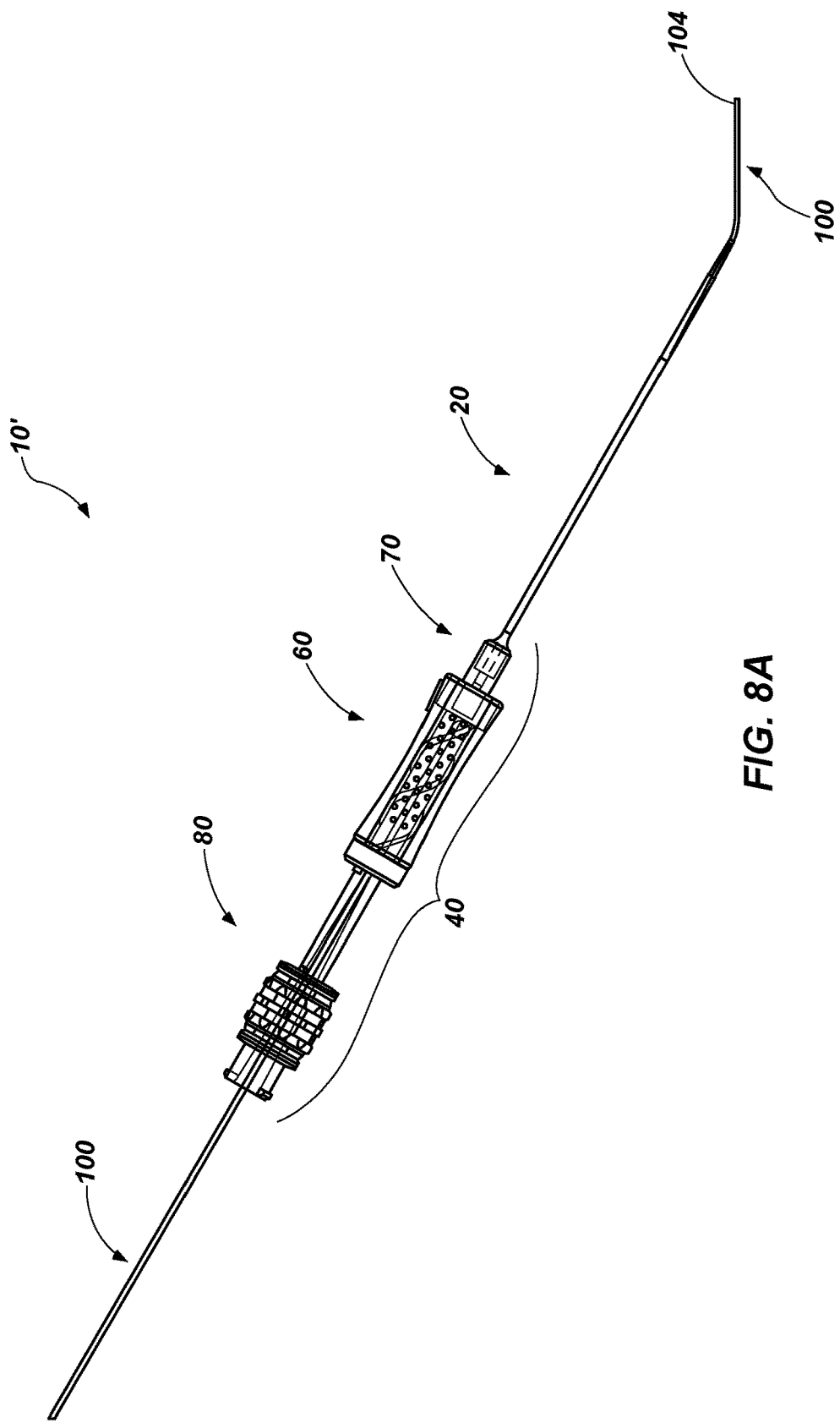

With reference to FIGS. 1-4, 3A and 4A, an embodiment of a percutaneous access system 10 according to this disclosure is depicted. The depicted percutaneous access system 10 comprises a trocar, which includes a cannula 20, a handle 40 and an obturator 50. The handle 40, which is secured to the cannula 20, may include a main body 60, a distal hub 70 and a proximal hub 80. The obturator 50 is configured for assembly with the handle 40 and the cannula 20.

The cannula 20 may be configured similarly to the microtaper needle of U.S. Pat. No. 7,803,142, the entire disclosure of which is incorporated herein by this reference. More specifically, the cannula 20 may include a proximal end 22 and a distal end 24. An expandable section 25 may extend proximally from the distal end 24 of the cannula 20 to an intermediate location along its length. The expandable section 25 may include a plurality of slits 26 (FIGS. 3, 5, 6, and 7) that extend through the thickness of a wall of the cannula 20, which extend along the length of the expandable section 25 and are spaced apart at different locations around the circumference of the expandable section 25. The slits 26 may separate the expandable section 25 into a plurality of expandable elements, which are also referred to herein as "leaves" 27.

In some embodiments, such as that depicted by FIGS. 1 and 2, the expandable section 25 may comprise a tapered portion of the cannula 20. More specifically, a proximal portion of the cannula 20 may have a constant outer diameter (i.e., it may be straight, or untapered), while the expandable section 25 or a portion thereof is tapered. As illustrated, an outer diameter of the cannula 20 may taper from a relatively large dimension at a proximal side of the taper (e.g. at a proximal side of the expandable section 25, etc.) to a smaller dimension at a distal side of the taper (e.g., at the distal end 24 of the cannula 20, etc.).

As illustrated by FIG. 5, an inner diameter of an expandable section 35 of an internal passageway 30, which resides within a tapered portion (e.g., the expandable section 25, etc.) of the cannula 20, may also include one or more tapers. In such an embodiment, as an elongated instrument 100 (FIGS. 7-8C) (e.g., a laparoscopic surgical instrument, a wire, a catheter, a tube, a sheath, etc.) with an outer diameter that exceeds the inner diameter of any portion of the expandable section 35 moves distally through the internal passageway 30, the elongated instrument 100 will force the leaves 27 outward, expanding the expandable section 25. Expansion of the expandable section 25 includes an effective expansion of the inner diameter of the expandable section 35 of the internal passageway 30 within the expandable section 25 of the cannula 20 and an increase in the outer diameter of the expandable section 25.

In some embodiments, tapering of the expandable section 35 of the internal passageway 30 that resides within the expandable section 25 of a cannula 20 may be varied. For example, the expandable section 35 of the internal passageway 30 may include at least one tapered portion and at least one straight portion. As another example, the expandable section 35 of the internal passageway 30 may include portions with different tapers. Without limitation, FIG. 5 illustrates an embodiment in which a proximal taper 36 of the expandable section 35 of an internal passageway 30 is configured to cause the expandable section 25 (FIGS. 1-4, 3A and 4A) of the cannula 20 (FIGS. 1 and 2) to expand in such a way that an outer diameter of the distal end 24 (FIGS. 1 and 2) of the cannula 20 increases to a first dimension, while a distal taper 37 (which may comprise an inner diameter that decreases from a proximal side of the distal taper 37 to a distal side of the distal taper 37) of the expandable section 35 of the internal passageway 30 may enable the expanded outer diameter of the distal end 24 of the cannula 20 to remain the same while an elongated instrument 100 (FIGS. 8A-8C) continues to advance distally through the internal passageway 30. Of course, other variations in the manner in which the expandable section 35 of the internal passageway 30 through the expandable section 25 of a cannula 20 tapers, as well as variations in the outer diameter of an elongated instrument 100 (FIGS. 7-8C) that may be moved through the expandable section 35 of the internal passageway 30, may enable the expandable section 25 of the cannula 20 to expand and/or collapse in any desired fashion as the elongated instrument 100 moves through the internal passageway 30, or at least through the expandable section 35 of the internal passageway 30.

With returned reference to FIGS. 1-4, 3A, 4A, and 7, a percutaneous access system 10 may include an elastic sleeve 28 that surrounds at least a proximal portion of the expandable section 25 of the cannula 20. In some embodiments, the elastic sleeve 28 may extend from a location at or adjacent to the proximal end 22 of the cannula 20 to a location somewhat proximal to the distal end 24 of the cannula 20. Without limitation, a distal end 29 of the elastic sleeve 28 may be located about 1 cm or about a quarter inch (¼ inch) proximal to the distal end 24 of the cannula 20.

The elastic sleeve 28 may be formed from a material that will enable it to conform to the shape and dimensions of the portions (e.g., a proximal portion of the expandable section 25, etc.) of the cannula 20 over which it is positioned. The material of the elastic sleeve 28, as well as its dimensions (e.g., its thickness, etc.), may enable the elastic sleeve 28 to expand while the expandable section 25 expands, and to contract upon removal of an expansion force (e.g., partial or complete removal of an elongated instrument 50, etc.) from the expandable section 25. As the elastic sleeve 28 contracts, it may force the leaves 27 of the expandable section 25 radially inward toward or to their original positions, thereby collapsing the expandable section 25 and, when the expansion force is totally removed therefrom, enabling the expandable section 25 to return to its collapsed state. The material from which the elastic sleeve 28 is formed, along with its dimensions, may also enable it to maintain its integrity when expanded and contracted, without significantly impeding insertion of the cannula 20 into and through a subject's skin. Suitable materials for use as the elastic sleeve 28 include, but are not limited to, dip molded elastomers and heat shrink elastomers, including elastomeric fluoropolymers. The thickness of the elastic sleeve 28 may be about 0.00025 inch to about 0.0025 inch (e.g., about 0.001 inch, etc.). FIGS. 6 and 7 respectively show an expandable section 25 of the cannula 20 in collapsed and expanded states.

As an alternative to the elastic sleeve 28, or in addition thereto, the expandable section 25 of the cannula 20 may be formed from a material that will resiliently return to its original shape (i.e., that will enable the leaves 27 to collapse) once an expansion force (e.g., an elongated instrument, etc.) is partially or completely removed from the expandable section 25.

As illustrated by FIGS. 2, 3, 3A, 4 and 4A, the obturator 50 of a trocar embodiment of a percutaneous access system 10 according to this disclosure includes a proximal end 52 and a distal end 54. The distal end 54 may be configured to fit within the internal passageway 30 through the cannula 20 and to be moved, or translated, along a length of the internal passageway 30, including through the expandable section 35 of the internal passageway 30. In the depicted embodiment, an outer diameter of a portion of the obturator 50 that resides within and/or is configured to be positioned within at least a portion of the internal passageway 30 through the cannula 20—i.e., a distal portion of the obturator 50—is uniform. In the embodiment of percutaneous access system 10 illustrated by FIGS. 1-4, 3A and 4A, the obturator 50 has an outer diameter that is the same as or slightly less than a smallest inner diameter of the internal passageway 30 through the cannula 20. Thus, as the obturator 50 is introduced into and through the internal passageway 30, and as the obturator 50 resides within the internal passageway 30, the obturator 50 will not cause the expandable section 25 of the cannula 20 to expand, thus enabling the expandable section 25 of the cannula 20 to remain in the collapsed state shown in FIGS. 5 and 6.

A proximal end 52 of the obturator 50 may be configured to engage or to be engaged by a corresponding feature of the handle 40 of the percutaneous access system 10. Without limitation, the proximal end 52 of the obturator 50 may be configured to engage or to be engaged by the proximal hub 80 of the handle 40 of the percutaneous access system 10.

As illustrated by FIG. 7, an elongated instrument 100 (e.g., a wire, a sheath, a tube, a catheter, etc.) with an outer diameter that exceeds the minimum inner diameter of the expandable section 35 of the internal passageway 30 through the cannula 20 will cause the expandable section 25 of the cannula 20 to expand. As the outer diameter of such an elongated instrument 100 is greater than the minimum inner diameter of the expandable section 35 of the internal passageway 30, introducing a distal end 104 of the elongated instrument 100 into the expandable section 35 will force to the leaves 27 of the expandable section 25 of the cannula 20 radially outward, enlarging the inner diameter of the expandable section 35 of the internal passageway 30 and expanding the outer diameter of the expandable section 25 of the cannula 20, particularly at its distal end 24.

Referring again to FIGS. 1-4, a further description of the manner in which the cannula 20 and the obturator 50 are assembled with one another, and a description of the manner in which the cannula 20 and the obturator 50 function relative to one another are provided. It should be noted that the teachings provided hereinafter are also applicable to the use of an elongated instrument 100 (FIGS. 7-8C) with the cannula 20, in place of the obturator 50.

The handle 40 of the percutaneous access system 10 may include a distal hub 70 at the proximal end 22 of the cannula 20 that may facilitate assembly of the obturator 50 or another elongated instrument 100 (FIGS. 7-8C) with the cannula 20. Specifically, the distal hub 70 may include a channel 76 that, at a distal side 74 of the distal hub 70, receives the proximal end 22 of the cannula 20. At a proximal side 72 of the distal hub 70, the channel 76 may be configured to enable alignment of the distal end 54 of the obturator 50 (or of another elongated instrument 100 (FIGS. 7-8C)) with the internal passageway 30 through the cannula 20.

The proximal side 72 of the distal hub 70 may also be configured to couple the cannula 20 to the main body 60 of the percutaneous access system 10. In a specific, but non-limiting embodiment, the proximal side 72 of the distal hub 70 may be configured to be received within an aperture 65 at a distal side 64 of the main body 60 of the handle 40, and may be fixedly coupled to the main body 60 (e.g., mechanically, with a suitable glue or cement, etc.).

The proximal side 62 of the main body 60 of the handle 40 may be configured to receive or otherwise engage a proximal hub 80 of the handle 40. More specifically, the distal portion 84 of the proximal hub 80 may be configured for receipt by an enlarged proximal portion of a passage 66 through the main body 60 of the percutaneous access system 10. With the main body 60 and the proximal hub 80 configured in this manner, when the proximal hub 80 is assembled with the main body 60, a channel 86 that extends through a length of the proximal hub 80 is aligned with and communicates with the passage 66 through the main body 60 and, thus, with the channel 76 that extends through the distal hub 70 and the internal passageway 30 that extends through the length of the cannula 20.

In the depicted embodiment, a retaining ring 69 may be configured to hold a distal-most end of the distal portion 84 of the proximal hub 80 in place within the passage 66 through the main body 60.

In some embodiments, features 85 (e.g., one or more spiral protrusions, or threads, etc.) on an outer circumference of the distal portion 84 may cooperate with (e.g., be received by, etc.) cooperating features 67 (e.g., one or more spiral grooves, etc.) on an inner circumference of the passage 66 through the main body 60. With such an arrangement, the movement of the distal portion 84 of the proximal hub 80 and, thus, the movement of the obturator 50 (or another elongated instrument 100 (FIGS. 7-8C) into and out of the distal end 24 of the cannula 20, may be controlled (e.g., by rotation of the proximal hub 80 relative to the main body 60, etc.).

In some embodiments, the distal portion 84 of the proximal hub 80, the retaining ring 69 and/or the passage 66 through the main body 60 may include one or more features 88, 68 that enable the proximal hub 80 to lock (rotationally and axially) in one or more positions (e.g., in a proximal position (i.e., with the obturator 50 or another elongated instrument 100 (FIGS. 7-8C) withdrawn (proximally) into the cannula 20), in one or more intermediate positions, in a distal position (i.e., with the obturator 50 or another elongated instrument 100 fully extended (distally) from the cannula 20), etc.).

On its proximal side 82, the proximal hub 80 may include one or more coupling features 83 configured to enable the percutaneous access system 10 to be secured to another apparatus. Without limitation, the coupling features 83 may comprise luer lock elements or other features that will enable the proximal hub 80 to be coupled to and uncoupled from a coupling element 53 with coupling features (not shown) at or near the proximal end 52 of the obturator 50 (FIG. 2), which correspond to the coupling features 83 at the proximal side 82 of the proximal hub 80 and which may fix the obturator 50 in place relative to a remainder of the percutaneous access system 10. Alternatively, or in addition, the coupling features 83 may enable another apparatus, such as an elongated instrument 100 (FIGS. 7-8C), to be secured in place relative to the proximal hub 80.

While FIGS. 1-4, 3A and 4A illustrate an embodiment of percutaneous access system 10 that includes a conventional, straight obturator 50 of a trocar, a percutaneous access system 10 according to this disclosure may also be adapted for use with a bendable obturator and/or a steerable obturator.

Turning now to FIGS. 8A-8C, once a percutaneous access system 10 has been used to access a desired location within a subject's body (e.g., a blood vessel, a cavity, etc.) and the distal end 24 of the cannula 20 is positioned at a desired location within the subject's body, the obturator 50 (FIGS. 2, 3, 3A, 4 and 4A) may be proximally drawn into the distal end 24 of the cannula 20 and removed (e.g., proximally withdrawn) from the internal passageway 30 through the cannula 20, from the channel 76 (FIG. 2) through the distal hub 70 of the handle 40, from the passage 66 (FIG. 2) through the main body 60 of the handle 40 and from the channel 86 (FIG. 2) through the proximal hub 80 of the handle 40, while the distal end 24 of the cannula 20 remains in place within the body of the subject. Removal of the obturator 50 from the cannula 20 and its handle 40 may make way for an elongated instrument 100, such as a wire, a sheath, a tube and/or a catheter, which may be used to further enable an elongated medical device (e.g., a catheter, etc.) to perform a medical procedure within the subject's body or to perform a medical procedure within the subject's body.

As illustrated by FIGS. 8A-8C, a percutaneous access system 10' may include a cannula 20, its handle 40 and an elongated instrument 100. With the distal end 24 of the cannula 20 of the percutaneous access system 10' at a desired location within the subject's body, a distal end 104 of the elongated instrument 100 may be introduced into the handle 40 through a proximal opening of the channel 86 (FIG. 1) that extends through the proximal hub 80. As the elongated instrument 100 is pushed distally into the handle 40, the distal end 104 of the elongated instrument 100 may move into and through the passage 66 (FIG. 1) through the main body 60 of the handle 40, into and through the channel 76 (FIG. 1) through the distal hub 70 of the handle 40 and then into and through the cannula 20. The distal end 104 of the elongated instrument 100 may then emerge from the distal end 24 of the cannula 20, at the desired location within the subject's body. Alternatively, a healthcare provider may distally push the elongated instrument 100 further, until the distal end 104 of the elongated instrument 100 is positioned at or near a targeted location within the subject's body (e.g., a location where a medical procedure is to take place, etc.).

Once the distal end 104 of the elongated instrument 100 is at the desired location or the targeted location, a proximal end (not shown) or an intermediate location of the elongated instrument 100 may be secured in place relative to the proximal hub 80 of the handle 40 of the percutaneous access system 10'. In some embodiments, the proximal hub 80 of the handle 40 of the percutaneous access system 10' may be manipulated in a manner that causes an engagement feature associated with the proximal hub 80 to engage the elongated instrument 100 at a location along a length of the elongated instrument 100. In a specific embodiment, the proximal hub 80 may be twisted about its access to cause an engagement feature thereof (e.g., an o-ring, a compressible tube, etc.) to abut and engage an exterior surface of the elongated instrument 100.

Alternatively, longer elongated instruments 100, including elongated instruments 100 that are to be introduced farther into a subject's body than is possible with the longitudinal movement provided by rotation of the proximal hub 80 relative to the main body 60 of the percutaneous access system 10', may merely be inserted through the channel 86 (FIG. 2) of the proximal hub 80, through the passage 66 (FIG. 2) through the main body 60, through the channel 76 of the distal hub 70 and through the internal passageway 30 (FIG. 2) that extends through the length of the cannula 20, which may enable manual longitudinal movement (e.g., with a healthcare provider's hand, etc.) of the elongated instrument 50 (FIGS. 1-3).

FIG. 8A shows the distal end 104 of the elongated instrument 100 protruding a relatively short distance beyond the distal end 24 of the cannula 20. FIG. 8B shows the distal end 104 of the elongated instrument 100 positioned a greater distance beyond the distal end of the cannula 20. FIG. 8C provides a close-up view of a bent portion 101 of the elongated instrument 100 shown in FIG. 8B.

From the foregoing, various uses of the percutaneous access system 10, 10', as disclosed above, should be apparent to those of ordinary skill in the art. In one embodiment of use, with returned reference to FIGS. 1-4, 3A and 3B, the distal end 54 of the obturator 50 may be inserted into the proximal end of the channel 86 through the proximal hub 80, through the channel 86, into and through the passage 66 through the main body 60, into and through the channel 76 that extends through the distal hub 70 and into and partially through the internal passageway 30 of the cannula 20. With the obturator 50 positioned in this manner (see FIGS. 2-4, 3A and 3B), the coupling element 53 at its proximal end 52 may engage the coupling features 83 on the proximal side 82 of the proximal hub 80 to fix the obturator 50 in place relative to a remainder of the percutaneous access system 10. With this arrangement, rotation of the proximal hub 80 relative to the main body 60 may enable the distal end 54 of the obturator 50 to be moved distally into and through the expandable section 25 of the cannula 20, and through the distal end 24 of the cannula 20, as shown in FIGS. 2-4, 3A and 4A. With the obturator 50 emerging or protruding from the distal end 24 of the cannula 20, its distal end 54 may be used to puncture the skin, another organ or other tissue of a subject. The distal end 24 of the cannula 20 may also be inserted into and through the subject's skin, another organ or other tissue. As the distal end 24 of the cannula 20 remains in place within the subject's body, in embodiments where the distal end 54 of the obturator 50 has been used to puncture a subject's skin, another organ or other tissue, the obturator 50 may be proximally retracted (e.g., by rotating the proximal hub 80 in the appropriate direction relative to the main body 60, etc.) and removed from the cannula 20 and the body 40.

With the distal end 24 of the cannula 20 remaining in position within the subject's body, another elongated instrument 100 (FIGS. 8A-8C) may be used with the cannula 20 and its handle 40 for any of a variety of medical procedures, including, but not limited to, procedures that require percutaneous access, such as vascular access procedures, laparoscopic procedures or the aspiration of fluid's from the subject's body (e.g., in biliary drainage, nephrostomy, abscess drainage and drainage of other fluids from other locations and/or sources).

Although the foregoing description sets forth many specifics, these should not be construed as limiting the scope of any of the claims, but merely as providing illustrations of some embodiments and variations of elements or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A percutaneous access system, comprising:
   a cannula with an internal passageway extending through a length thereof, the internal passageway including a tapered section within an expandable section at a distal portion of the cannula, the expandable section including a plurality of leaves that are circumferentially adjacent to one another and that are capable of being forced radially outward from one another;
   an obturator capable of coaxial movement through the internal passageway through the cannula; and
   a handle secured to a proximal end of the cannula, the handle including a channel capable of receiving the obturator, the handle further including:
      a distal hub at a fixed location relative to the proximal end of the cannula;
      a main body proximal to the distal hub, the distal hub secured to a distal end of the main body; and a proximal hub coupled to the main body in a manner that enables selective rotation of the proximal hub relative to the main body and the distal hub, selective longitudinal movement of the proximal hub toward and/or away from the main body and the distal hub, and fixed coupling of the proximal hub to a coupling element at a proximal end of the obturator such that rotational movement and/or longitudinal movement of the proximal hub relative to the distal hub causes the obturator to be driven rotationally and/or longitudinally within the internal passageway through the cannula.

2. The percutaneous access system of claim 1, wherein a distal portion of the obturator is capable of being positioned within the internal passageway and to extend through a distal end of the cannula without forcing the plurality of leaves of the expandable section radially outward.

3. The percutaneous access system of claim 1, further comprising:
an elongated instrument capable of being positioned within the internal passageway through the cannula and, as the elongated instrument extends into and/or through a portion of the internal passageway through the distal portion of the cannula, to force the leaves of the expandable section radially outward.

4. The percutaneous access system of claim 3, wherein the proximal hub is capable of driving the elongated instrument rotationally within the internal passageway through the cannula and/or longitudinally through the internal passageway of the cannula.

5. The percutaneous access system of claim 3, wherein the elongated instrument comprises a bendable elongated instrument and/or a steerable elongated instrument.

6. The percutaneous access system of claim 3, wherein the handle is capable of locking the elongated instrument into place in at least one position along the length of the cannula.

7. The percutaneous access system of claim 6, wherein the handle is capable of locking the elongated instrument into place in a distal-most position, in which a distal end of the elongated instrument protrudes beyond a distal end of the cannula.

8. The percutaneous access system of claim 1, wherein the obturator comprises a bendable obturator and/or a steerable obturator.

9. The percutaneous access system of claim 1, wherein the handle is capable of locking the obturator into place in at least one position along the length of the cannula.

10. The percutaneous access system of claim 9, wherein the handle is capable of locking the obturator into place in a distal-most position, in which a distal end of the obturator protrudes beyond a distal end of the cannula.

11. A percutaneous access system, comprising:
a cannula with an internal passageway extending through a length thereof, the internal passageway including a tapered section within an expandable section at a distal portion of the cannula, the expandable section including a plurality of leaves that are circumferentially adjacent to one another and that are capable of being forced radially outward from one another;
an obturator capable of coaxial movement through the internal passageway through the cannula;
a handle secured to a proximal end of the cannula, the handle including a channel capable of receiving the obturator, the handle further including:
a distal hub at a fixed location relative to the proximal end of the cannula;
a main body proximal to the distal hub, the distal hub secured to a distal end of the main body; and
a proximal hub coupled to the main body in a manner that enables selective rotation of the proximal hub relative to the main body and the distal hub, selective longitudinal movement of the proximal hub toward and/or away from the main body and the distal hub, and fixed coupling of the proximal hub to a coupling element at a proximal end of the obturator such that rotational movement and/or longitudinal movement of the proximal hub relative to the distal hub causes the obturator to be driven rotationally and/or longitudinally within the internal passageway through the cannula; and
an elastic sleeve over a proximal portion of the expandable section of the cannula, the elastic sleeve capable of causing the plurality of leaves to resiliently collapse.

12. The percutaneous access system of claim 11, wherein a distal portion of the obturator is capable of extending into and through a portion of the internal passageway that extends through a distal end of the cannula without forcing the plurality of leaves of the expandable section radially outward.

13. The percutaneous access system of claim 11, further comprising:
an elongated instrument capable of being positioned within the internal passageway through the cannula and, as the elongated instrument extends into and/or through a portion of the internal passageway through a distal end of the cannula, to force the plurality of leaves of the expandable section radially outward.

14. The percutaneous access system of claim 13, wherein the elastic sleeve is capable of causing the plurality of leaves to resiliently collapse as the elongated instrument is withdrawn from the portion of the internal passageway that extends through the distal end of the cannula.

15. A percutaneous access system, comprising:
a cannula with an internal passageway extending through a length thereof, the internal passageway including a tapered section within an expandable section at a distal portion of the cannula, the tapered section including a plurality of different tapers, the expandable section including a plurality of leaves that are circumferentially adjacent to one another and that are capable of being forced radially outward from one another; and
a handle secured to a proximal end of the cannula, the handle including a channel for receiving an elongated medical device, the handle further including:
a distal hub at a fixed location relative to the proximal end of the cannula;
a main body proximal to the distal hub, the distal hub secured to a distal end of the main body; and
a proximal hub coupled to the main body in a manner that enables selective rotation of the proximal hub relative to the main body and the distal hub, selective longitudinal movement of the proximal hub toward and/or away from the main body and the distal hub, and fixed coupling of the proximal hub to a coupling element at a proximal end of an elongated medical device that has been inserted into the channel of the main body such that rotational movement and/or longitudinal movement of the proximal hub relative to the distal hub causes the elongated medical device to be driven rotationally and/or longitudinally within the internal passageway through the cannula.

* * * * *